United States Patent
Ankeney et al.

(10) Patent No.: US 8,232,812 B2
(45) Date of Patent: Jul. 31, 2012

(54) CORROSION TESTING METHOD

(75) Inventors: Scott Michael Ankeney, Ann Arbor, MI (US); Brian F. Smith, Canton, MI (US)

(73) Assignee: Toyota Motor Engineering & Manufacturing North America, Inc., Erlanger, KY (US)

( * ) Notice: Subject to any disclaimer, the term of this patent is extended or adjusted under 35 U.S.C. 154(b) by 328 days.

(21) Appl. No.: 12/708,622

(22) Filed: Feb. 19, 2010

(65) Prior Publication Data

US 2011/0204904 A1 Aug. 25, 2011

(51) Int. Cl.
*G01R 27/08* (2006.01)
*G01N 27/26* (2006.01)
*G01N 17/04* (2006.01)

(52) U.S. Cl. ............... 324/700; 204/404; 205/775.5
(58) Field of Classification Search ............. 324/700, 324/71.2; 204/404, 400; 205/775.5, 647, 205/640; 73/86
See application file for complete search history.

(56) References Cited

U.S. PATENT DOCUMENTS

| | | | |
|---|---|---|---|
| 3,197,724 A | 7/1965 | Marsh | |
| 4,190,502 A * | 2/1980 | Kanno et al. | 205/775.5 |
| 4,780,664 A * | 10/1988 | Ansuini et al. | 324/700 |
| 4,863,571 A | 9/1989 | Chambaere | |
| 5,045,775 A | 9/1991 | White et al. | |
| 6,365,034 B1 | 4/2002 | Spellane | |
| 7,388,386 B2 * | 6/2008 | Ramgopal et al. | 324/700 |

* cited by examiner

*Primary Examiner* — Hoai-An D Nguyen
(74) *Attorney, Agent, or Firm* — Gifford, Krass, Sprinkle, Anderson & Citkowski, P.C.

(57) ABSTRACT

The present invention discloses a process for determining which material within a vicinity of an electrically conducting material is causing corrosion of the electrically conducting material. The process includes providing a piece of electrically conducting material, a piece of potentially corrosive material that is present in the vicinity of the electrically conducting material, an electrical resistance measuring device and a testing chamber. Thereafter, the piece of electrically conducting material and the piece of potentially corrosive material are placed within the testing chamber and the electrical resisting measuring device monitors the electrical resistance of the piece of electrically conducting material as a function of time.

19 Claims, 2 Drawing Sheets

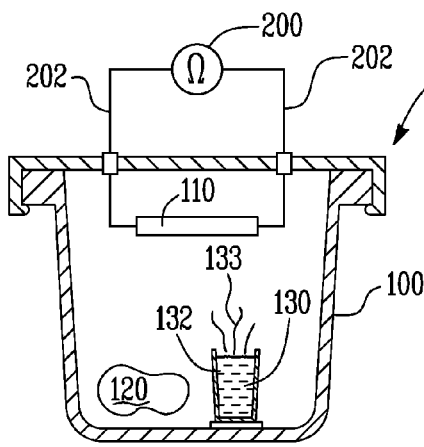
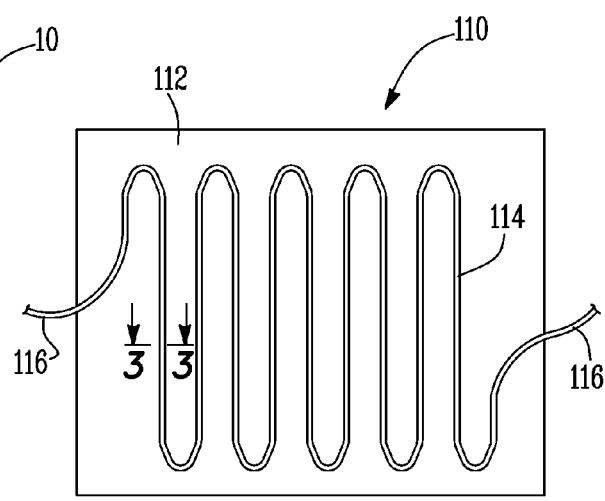
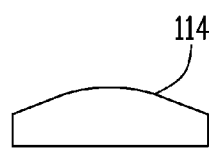
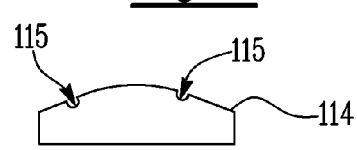
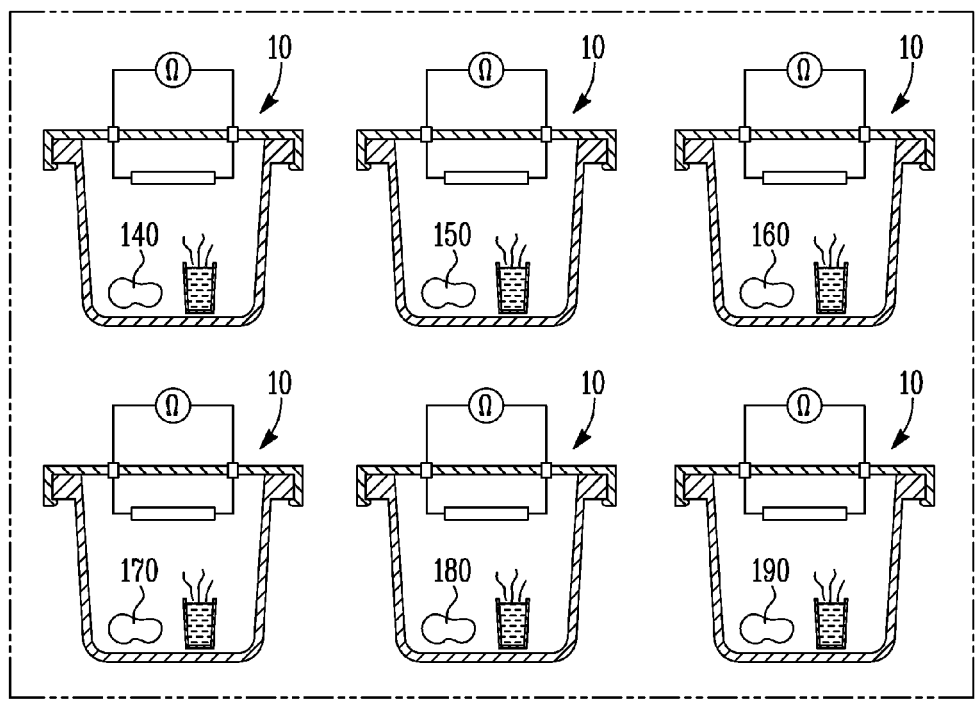

CORROSION TESTING METHOD

FIELD OF THE INVENTION

The present invention is related to a corrosion testing method, and in particular, to a corrosion testing method for determining which material among a plurality of different materials in a given environment is causing corrosion of an electrically conducting material also within the environment.

BACKGROUND OF THE INVENTION

The use of heating elements or heating grids to remove fog, frost, and the like from windows is known in the art. In particular, it is not uncommon for a "heating grid" made from a thin strip or wire of electrically conductive material to be present on a rear window of a motor vehicle.

The heating grid is typically in electrical communication with a power source that can afford for an electrical current to pass through the electrically conductive material and the material increasing in temperature as the current passes therethrough. In this manner, rear window glass can be heated so evaporation of fog, melting of frost, and the like can occur. In some instances, the heating grid can be screen printed onto the glass and can contain elements such as silver, gold, copper, etc.

One or more locations of the heating grid can experience corrosion if materials within the vicinity of the heating grid come into contact therewith and/or release an element and/or compound that when in contact with the grid results in corrosion. In addition, if water vapor is present in the environment, corrosion can be enhanced by the reaction of the material, element and/or compound with the water vapor to form a corrosive agent.

Determining which material in the vicinity of the heating grid is causing the corrosion can be difficult. For example, within the interior of a motor vehicle, a multitude of materials such natural fabrics, polymers and the like are present and determining which material is ultimately responsible for corrosion of the heating grid can require a plurality of time consuming and/or cost prohibitive testing.

For example, heretofore testing procedures have required performing a chemical analysis of the variety of materials in the vicinity of the heating grid, determining which material might possibly have a corrosive element, and testing the material of the heating grid in a specialized corrosion test containing the corrosive element. Therefore, a corrosion test that provides for simple and yet effective determination of which material in the vicinity of a heating grid can cause corrosion of the grid would be desirable.

SUMMARY OF THE INVENTION

The present invention discloses a process for determining which material within a vicinity of an electrically conducting material can provide a corrosion agent that affords corrosion of the electrically conducting material. The process includes providing a piece of electrically conducting material, a piece of potentially corrosive material that is present in the vicinity of the electrically conducting material, an electrical resistance measuring device and a testing chamber. Thereafter, the piece of electrically conducting material and the piece of potentially corrosive material are placed within the testing chamber and the electrical resistance measuring device is electrically connected across the piece of electrically conducting material.

Monitoring of the electrical resistance across the piece of electrically conducting material as a function of time affords for determination of whether or not the piece of potentially corrosive material within the testing chamber is providing a corrosion agent that affords corrosion of the electrically conducting material. In particular, an increase in the electrical resistance as a function of time across the piece of electrically conducting material can indicate a reduction of a cross section of the conductive material caused by corrosion thereof. In the alternative, if there is no increase in the electrical resistance across the piece of electrically conducting material as a function of time, then corrosion of the electrically conducting material is not occurring.

In some instances, the piece of electrically conducting material can be at least part of a heating grid attached to a piece of glass. The piece of glass may or may not be part of a rear window of a motor vehicle, and thus the heating grid can be at least part of a rear window defogger. The piece of potentially corrosive material can be a fabric used within an interior of the motor vehicle and the corrosion agent can be sulfur. In addition, water vapor can be provided within the testing chamber and the corrosion agent can react with the water vapor to form one or more chemical species that attacks and/or corrodes the heating grid.

The process can include providing a plurality of heating grid elements, a plurality of different materials used, or to be used, within the interior of a motor vehicle, and placing one heating grid element and one or more of the materials within a testing chamber. In this manner, a plurality of corrosion tests can be performed simultaneously and a material that is present, or will be present, within the interior of the motor vehicle and provides a corrosion agent can be identified.

BRIEF DESCRIPTION OF THE DRAWINGS

FIG. 1 is a schematic illustration of a testing apparatus according to an embodiment of the present invention;

FIG. 2 is a schematic representation of a heating grid attached to a piece of glass;

FIG. 3a is a cross-sectional view of section 3-3 shown in FIG. 2;

FIG. 3b is the cross section shown in FIG. 3a with corrosion of the heating grid illustrated thereon;

FIG. 4 is a schematic representation of a plurality of testing apparatus according to an embodiment of the present invention.

DETAILED DESCRIPTION OF THE INVENTION

Figure 5:
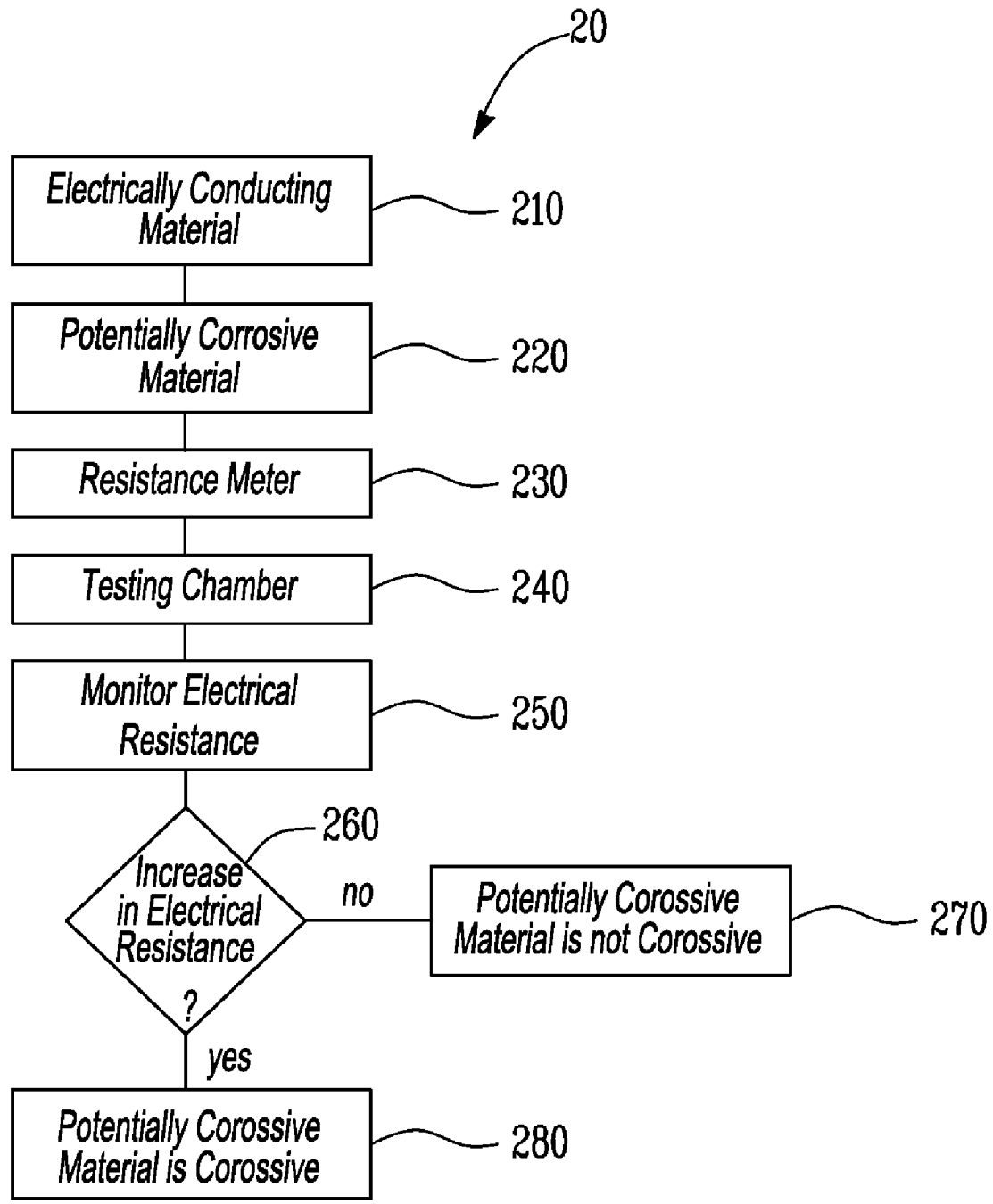
FIG. 5 is a flowchart illustrating a process according to an embodiment of the present invention.

The present invention discloses an apparatus and a process for determining which material within a given environment is providing a corrosion agent and affording for corrosion of a piece of electrically conducting material. The process includes providing a testing chamber, a piece of the electrically conducting material, a piece of potentially corrosive material and an electrical resistance measuring device. The piece of electrically conducting material is placed within the testing chamber along with the piece of potentially corrosive material and the resistance across the electrically conducting material is monitored as a function of time.

In some instances, the testing chamber can be a closed environment and may or may not have water vapor therewithin. When an increase in the electrical resistance of the piece of electrically conducting material is observed, the piece of potentially corrosive material has provided a corrosion agent, the corrosion agent has come into contact with and chemically reacted with the piece of electrically conducting material and corrosion has or is occurring. It is appreciated that corrosion of the electrically conductive material can reduce a cross section thereof and thus afford for the increase of electrical resistance across the material. In the alternative, if the electrical resistance of the piece of electrically conducting material does not increase as a function of time, then the piece of potentially corrosive material has not provided a corrosion agent and corrosion of the material has not or is not occurring.

The piece of electrically conducting material can be at least part of a heating grid for use as a window defogger and the heating grid may or may not be attached to a piece of glass. It is appreciated that a window defogger can also be known as a window heater, window deicer and the like. The piece of potentially corrosive material can be one of a plurality of different materials that are present in the vicinity of the heating grid during its operation. For example and for illustrative purposes only, the heating grid can be attached to a rear window of a motor vehicle and the piece of potentially corrosive material can be a piece of fabric, component and the like that is present within the interior of the motor vehicle. The piece of fabric can be a sulfur-containing fabric such that the corrosion agent is sulfur and the sulfur reacts with water vapor to form a sulfuric chemical species that corrodes the heating grid. The heating grid can contain silver and may or may not be screen printed onto the piece of glass.

Turning now to FIG. 1, a testing apparatus according to an embodiment of the present invention is shown generally at reference numeral 10. The testing apparatus 10 can include a testing chamber 100, a piece of electrically conducting material 110 and a piece of potentially corrosive material 120. Optionally, a container 130 having a liquid 132 therewithin can provide a vapor 133 within the testing chamber 100. It is appreciated that any liquid 132 can be included, for example a liquid that is known to be present in the same environment as the piece of electrically conducting material 110. As such, liquids such as water, gasoline, diesel fuel, paint, radiator antifreeze, and the like can be present. The testing apparatus 10 can also include an electric resistance measuring device 200 with a pair of leads 202 that afford for the measurement of electrical resistance across the piece of electrically conducting material 110. For the purposes of the present invention, the term "across the piece of electrically conducting material" is defined or used to describe measurement of the electrical resistance along the longest dimension of the piece of material.

In some instances, the piece of electrically conducting material can be at least a portion of a heating grid as illustratively shown in FIG. 2. The heating grid can include an elongated serpentine piece of electrically conducting material 114 with a pair of leads 116 connected thereto. The electrically conducting material 114 can be attached to a piece of glass 112 by screen printing, painting, and the like. It is appreciated that the elongated piece of electrically conducting material 114 has a generally thin cross section as shown in FIG. 3A which illustrates an end view of section 3-3 shown in FIG. 2. It is also appreciated that the cross section shown in FIG. 3A is for illustrative purposes only and the exact shape can be different than shown.

In other instances, the piece of electrically conducting material 110 does not have to be connected to the electric resistance device 200 using the pair of leads 202 as shown in FIG. 1. For example, the piece of electrically conducting material 110 can be placed in the testing chamber 100 with the piece of potentially corrosive material 120 without being connected with the leads 202, and at a predetermined time of exposure/testing, removed from the testing chamber 100 in order to have its electrical resistance measured using the device 200. After measuring the electrical resistance of the piece of electrically conducting material 110, the corrosion test can be terminated or the piece of material 110 can be placed back into the testing chamber 100 for additional exposure therewithin.

FIG. 3A illustrates an un-corroded cross section of a portion of the heating grid whereas FIG. 3B illustrates a cross section after corrosion at locations 115 has occurred and reduced the cross section of the material. With a reduction in cross section at such a location, the resistance across or through the elongated electrically conducting material 114 will increase. As such, monitoring of the electrical resistance exhibited by the heating grid can afford for detection of corrosion thereof.

In some instances, the liquid 132 can be and thereby result in the vapor 133 being water vapor. In addition, the piece of potentially corrosive material can be a piece of fabric that contains sulfur. The sulfur can evaporate, sublimate, etc. from the piece of material 120, react with the water vapor, and produce a chemical species such as sulfuric acid. The sulfuric acid can come into contact with the heating grid 114, cause corrosion thereof and thereby result in an increase of the electrical resistance across the grid 114. It is appreciated that such an environment within the testing chamber 100 can simulate the interior of a motor vehicle and thus be used to determine whether or not a piece of fabric that is in use, or plans to be used, within the interior may cause corrosion problems of electrically conducting material(s) such as the heating grid for a rear window defogger.

In some instances, the testing apparatus 10 can be used to conduct a plurality of corrosion tests simultaneously with a different piece of material placed within the testing chamber 100. For example, as shown in FIG. 4, different pieces of potentially corrosive material 140-190 can be placed in different testing chambers 100. In this manner, which of the materials 140-190 that is causing, or potentially could cause, corrosion can be identified. It is appreciated that more than one piece of material 140-190 can be placed within a single testing chamber 100 in order to determine if a combination of materials is responsible, or could be responsible, for corrosion of the electrically conducting material 110 such as the heating grid 114.

Turning now to FIG. 5, a schematic diagram illustrating possible steps of a process for determining a corrosive material used in an environment where an electrically conducting material is present is shown generally at reference numeral 20. The process 20 can include providing a piece of electrically conducting material at step 210, providing a piece of potentially corrosive material at step 220, and providing an electrical resistance meter such as an ohmmeter at step 230. In addition, a testing chamber can be provided at step 240, and the piece of electrically conducting material 210 and the piece of potentially corrosive material 220 can be placed within the testing chamber. Thereafter, the electrical resistance across the electrically conducting material can be monitored as a function of time at step 250. As indicated at step 260, whether or not the electrical resistance across the electrically conducting material increases is determined. An increase in the electrical resistance indicates that the potentially corrosive material is corrosive at step 280 while no increase in the electrical resistance can indicate that the potentially corrosive material is not corrosive as shown at step 270.

As indicated in FIG. 4, a plurality of testing chambers can be provided and one of a plurality of potentially corrosive materials can be placed in each testing chamber. Also, the electrical resistance of the electrically conducting material can be monitored for each testing chamber in order to simply and reliably determine which of the potentially corrosive materials does in fact cause corrosion of the electrically conducting material. In addition, a testing chamber with a piece of electrically conducting material and a piece of potentially corrosive material can be heated and/or raised to an elevated temperature in order to better simulate an operational condition and/or accelerate corrosion of the piece of electrically conducting material. It is appreciated that the heating can be accomplished using any method, device, etc., known to those skilled in the art, illustratively including the use of a resistance heated oven, a heat lamp, a microwave oven and the like.

It is further appreciated that the electrical resistance of a piece of electrically conducting material is a function of the temperature of the material, and as such, resistance measurements should be take at a single, or at a generally single temperature. For example and for illustrative purposes only, electrical resistance measurements can be taken while the piece of electrically conducting material is at an elevated testing temperature, after the piece of electrically conducting material has been cooled to room temperature, a constant temperature in between, and the like.

The invention is not restricted to the illustrative examples described above. The examples, embodiments, etc. are not intended as limitations on the scope of the invention. Processes, apparatus, compositions, and the like described herein are exemplary and not intended as limitations on the scope of the invention. Changes herein and other uses will occur to those skilled in the art. The scope of the invention is defined by the scope of the claims.

We claim:

1. A process for determining a corrosive material in an interior of a motor vehicle, the process comprising:
   providing a piece of electrically conducting material;
   providing a piece of potentially corrosive material used within an interior of a motor vehicle;
   providing an electrical resistance measuring device;
   providing a testing chamber;
   placing the piece of electrically conducting material and the piece of potentially corrosive material in the testing chamber;
   electrically connecting the piece of electrically conducting material to the electrical resistance measuring device;
   monitoring an electrical resistance of the piece of electrically conducting material as a function of time;
   wherein an increase in the electrical resistance across the piece of electrically conducting material is a result of a corrosion agent being released from the piece of potentially corrosive material, coming into contact and chemically reacting with the piece of electrically conducting material, and corroding and reducing a cross section of the piece of electrically conducting material; and
   no increase in the electrical resistance of the piece of electrically conducting material is a result of a corrosive element not being released from the piece of potentially corrosive material and the piece of electrically conducting material not having a reduction in the cross section due to corrosion.

2. The process of claim 1, wherein the piece of electrically conducting material contains silver.

3. The process of claim 2, wherein the piece of electrically conducting material is at least a portion of a heating grid for a window defogger.

4. The process of claim 3, wherein the at least a portion of the heating grid is attached to a piece of glass.

5. The process of claim 4, wherein the piece of glass is part of a rear window of the motor vehicle.

6. The process of claim 1, wherein the piece of potentially corrosive material is a piece of fabric used within the interior of the motor vehicle.

7. The process of claim 6, wherein the corrosion agent is sulfur.

8. The process of claim 7, further comprising providing water vapor within the testing chamber.

9. The process of claim 8, wherein the water vapor chemically reacts with the sulfur released from the piece of fabric to produce sulfuric acid, the sulfur acid coming into contact with and corroding the piece of electrically conducting material.

10. The process of claim 9, wherein corroding of the piece of electrically conducting material reduces a cross section of the piece of electrically conducting material and causes the electrical resistance across the piece of electrically conducting material to increase.

11. A process for determining a corrosive material in an interior of a motor vehicle, the process comprising:
    providing a plurality of pieces of electrically conducting material;
    providing a plurality of different materials used within an interior of a motor vehicle;
    providing an electrical resistance measuring device;
    providing a plurality of testing chambers;
    placing one of the plurality of pieces of electrically conducting material and one of the plurality of different materials used within the interior of the motor vehicle into each of the plurality of testing chambers such that each testing chamber has a piece of the electrically conducting material and a piece of material used within the interior of the motor vehicle;
    electrically connecting the electrical resistance measuring device to each of the pieces of electrically conducting material and measuring the electrical resistance across the piece;
    monitoring the electrical resistance of each piece of electrically conducting material as a function of time;
    determining which piece of electrically conducting material has an increase in electrical resistance with increasing time.

12. The process of claim 11, wherein the plurality of pieces of electrically conducting material contain silver.

13. The process of claim 12, wherein each of the plurality of pieces of electrically conducting material are at least a portion of a heating grid for a window defogger attached to a piece of glass.

14. The process of claim 13, wherein the piece of glass is part of a rear window of the motor vehicle.

15. The process of claim 1, wherein the piece of potentially corrosive material is a piece of fabric used within the interior of the motor vehicle.

16. The process of claim 15, wherein the piece of potentially corrosive material used within the interior of the motor vehicle that is within the testing chamber containing the piece of electrically conducting material that has an increase in electrical resistance with increasing time releases a corrosion agent during testing.

17. The process of claim 16, wherein the corrosion agent is sulfur.

18. The process of claim 16, further comprising providing water vapor within each of the plurality of testing chambers.

19. The process of claim 18, wherein the water vapor chemically reacts with the sulfur to produce sulfuric acid, the sulfuric acid coming into contact with and corroding the piece of electrically conducting material.

* * * * *